US006613754B1

(12) United States Patent
Wu

(10) Patent No.: US 6,613,754 B1
(45) Date of Patent: Sep. 2, 2003

(54) POLYSACCHARIDE-BASED EXTRACT FROM GANODERMA, PHARMACEUTICAL USE THEREOF, AND PROCESS FOR PREPARING THE SAME

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 120 days.

(21) Appl. No.: 09/667,735

(22) Filed: Sep. 22, 2000

(51) Int. Cl.$^7$ .................. A61K 31/715; C07H 1/08; C08B 37/00

(52) U.S. Cl. .................. 514/54; 536/128; 435/274

(58) Field of Search .................. 514/54; 435/274; 536/128

(56) References Cited

U.S. PATENT DOCUMENTS

| | | | |
|---|---|---|---|
| 4,051,314 A | * 9/1977 | Ohtsuka et al. | 536/1.11 |
| 5,334,704 A | * 8/1994 | Tsunoo et al. | 530/371 |
| 5,574,023 A | * 11/1996 | Shibata et al. | 514/54 |
| 5,997,875 A | * 12/1999 | Zhou et al. | 424/195.1 |

FOREIGN PATENT DOCUMENTS

| | | | |
|---|---|---|---|
| JP | 405194175 A | * | 8/1993 |
| JP | 09056362 A | * | 3/1997 |

OTHER PUBLICATIONS

Hong et al, "Purification and Characterization of Polysaccharide from *Ganoderma Lucidum* Fermentative Product", Shanghai Jiaotong Daxue Xuebao (1994), vol. 28, No. 2, pp. 83–89.*

Chemical & Pharmaceutical Bulletin, 29(12);3611–6, 1981 (Abstract only).

Anticancer Research, 12(4):1211–5, 1992 (Abstract only).

Japanese Journal of Pharmacology, 59(2):171–6, 1992 (Abstract only).

Bioscience, Biotechnology & Biochemistry, 57(6):894–900, 1993 (Abstract only).

Bioscience, Biotechnology & Biochemistry, 58(7):1202–5, 1994 (Abstract only).

International Journal of Cancer, 70(6):699–705, 1997 (Abstract only).

Biological & Pharmaceutical Bulletin, 20(4):417–20, 1997 (Abstract only).

* cited by examiner

*Primary Examiner*—James O. Wilson
*Assistant Examiner*—Everett White
(74) *Attorney, Agent, or Firm*—Morgan & Finnegan, LLP

(57) ABSTRACT

In a process for preparing a polysaccharide-based extract, raw material of ganoderma genus is subjected to an alcohol treatment to obtain a polysaccharide-rich product from which a supernatant solution is subsequently obtained with the use of water of an elevated temperature as an extracting agent. Thereafter, alcohol is added to the supernatant solution to precipitate the polysaccharide-based extract. The polysaccharide-based extract can be used in an orally active medicinal product which has immunopotentiating and antitumoral effects.

6 Claims, 6 Drawing Sheets

POLYSACCHARIDE-BASED EXTRACT FROM GANODERMA, PHARMACEUTICAL USE THEREOF, AND PROCESS FOR PREPARING THE SAME

FIELD OF THE INVENTION

The present invention relates to a process for preparing a polysaccharide-based extract from *Ganoderma lucidum* or *Ganoderma tsugae*. Particularly, this invention relates to a use of the polysaccharide-based extract of Ganoderma herbal material as an orally active medicinal product which has immunopotentiating and antitumoral effects.

BACKGROUND OF THE INVENTION

Polysaccharide-based extracts of *Ganoderma lucidum* or *Ganoderma tsugae* have been studied for years for their medicinal effects in immunopotenciation and antitumoral activity. For example, in Chemical & Pharmaceutical Bulletin. 29(12): 3611–6, 1981 December, a water-soluble antitumor polysaccharide of *Ganoderma lucidum* has been studied as to its structure. In Anticancer Research 12(4): 1211–5, 1992 July–August, the effect of *Ganoderma lucidum* on induction of differentiation in leukemic U937 cells has been discussed. In Japanese Journal of Pharmacology, 59(2):171–6, 1992 June, water-soluble extract of *Ganoderma tsugae* is indicated to possess an enhanced splenic natural killer cell activity, and a desirable effect in serum interferon production. It was also reported in Bioscience, Biotechnology & Biochemistry, 57(6):894–900, 1993 June, that the fruiting body of *Ganodernma tsugae*, the Chinese mushroom Songshan Lingzhi, was subjected to the systemic treating process, i.e. extraction, fractionation, and purification, to obtain polysaccharides which have antitumoral activity. Other studies concerning water-soluble polysaccharides extracted from *Ganoderma lucidum* or *Ganoderma tsugae* can be found in Bioscience, Biotechnology & Biochemistry, 58(7): 1202–5, 1994 July; in International Journal of Cancer, 70(6):699–705, Mar. 17, 1997; and in Biological & Pharmaceutical Bulletin, 20(4):417–20, 1997 April. It might be due to the fact that most of the water-soluble polysaccharides as reported above, which were investigated as to the antitumoral and immunomodulating activities, have been extracted in the presence of sodium hydroxide solution, no significant effectiveness in antitumoral and immunomodulating activities have been reported when the water-soluble polysaccharides were administered via alimentary route. All the reports teaching and demonstrating the antitumoral and immunomodulating effects of water-soluble polysaccharides extracted from *Ganoderma lucidum* or *Ganoderma tsugae* were based on the effects exhibited by the intake of ganoderma extract via a parenteral route.

It is believed that the presence of sodium hydroxide solution in the extraction of polysaccharide gives rise to the smaller dimension of the polysaccharide molecules in the resultant extract. The polysaccharide molecules of smaller dimension in the ganoderma extract of the prior methods evidently account for the unavailability in reporting the antitumoral and immunomodulating effectiveness of the ganoderma extract when the latter is administered orally.

U.S. Pat. No. 5,721,134 issued to Kwon Hseng Lee et al., taught a proteoglycan G 009 which was extracted from *Ganoderma lucidum* IY 009, and which possesses antitumoral and immunostimulating effects. The demonstration of such effects is also based on the dosage intake via a parenteral route.

SUMMARY OF THE INVENTION

It is an object of this invention to provide a process for preparing a polysaccharide-based extract from *Ganoderma lucidum* or *Ganoderma tsugae* which can be used in an orally active medicinal product having antitumoral and immunopotentiating effects.

It is an another object of this invention to provide a pharmaceutical composition manufactured by the process according to the present invention. In the experiments performed in this invention, the inventor unexpectedly found that said pharmaceutical composition can be orally administered while retaining the desired activities in antitumoral and immunopotentiating effects.

In accordance with this invention, the process for preparing a polysaccharide-based extract consists essentially the steps of:

(1) subjecting a raw ganoderma herbal material to an alcohol treatment to remove a major portion of non-polysaccharide ingredients to obtain a polysaccharide-rich product;

(2) using water of an elevated temperature as an extracting agent for the polysaccharide-rich product to obtain a supernatant solution; and (3) adding an alcohol into the supernatant solution to precipitate the polysaccharide-based extract.

BRIEF DESCRIPTION OF THE DRAWINGS

The above and other objects and features of the present invention will become apparent with reference to the following description of the preferred embodiments taken in conjunction with the accompanying drawings, in which.

DETAILED DESCRIPTION OF THE PREFERRED EMBODIMENTS

Figure 1:
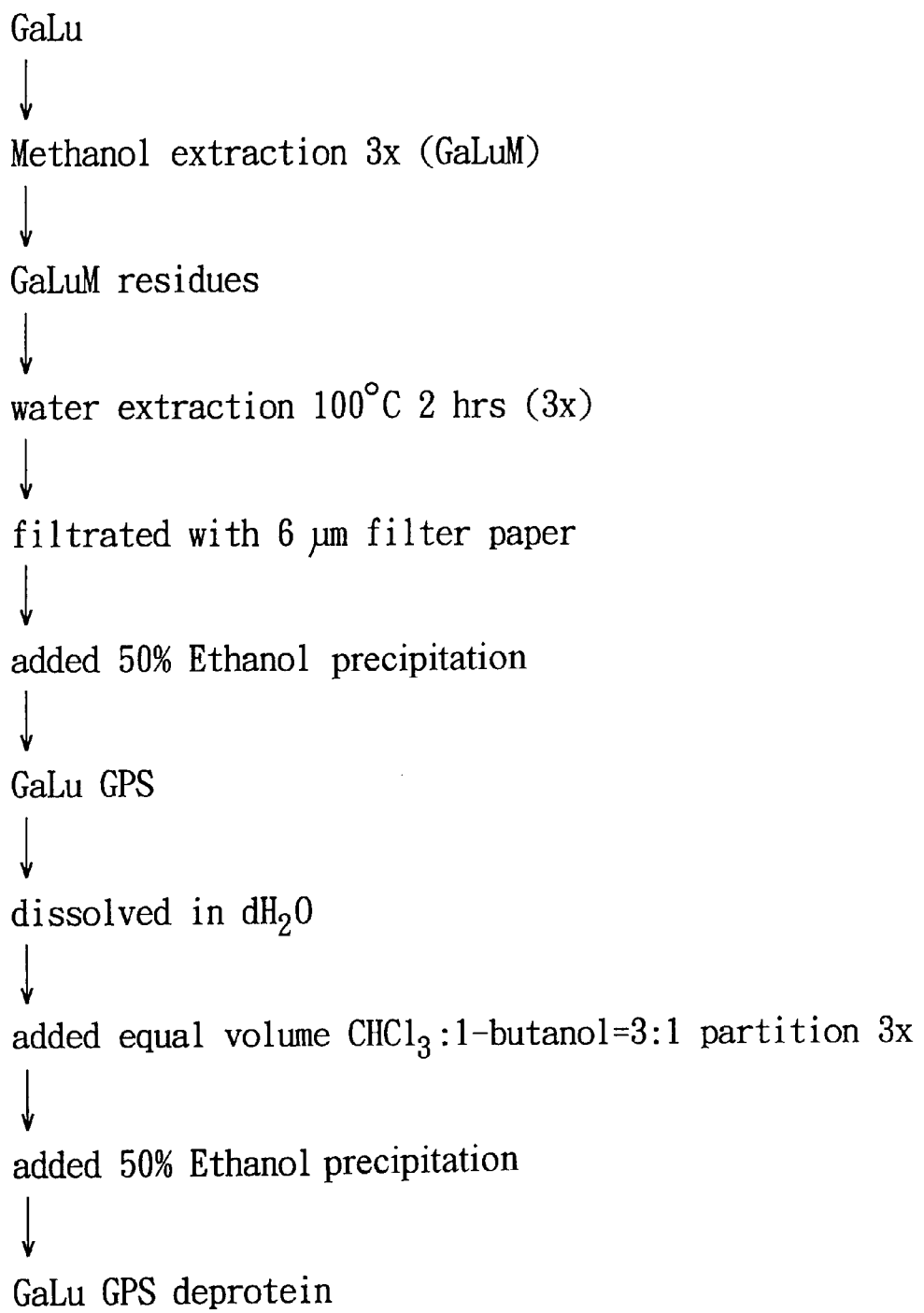
FIG. 1 is an isolation flowchart for the orally-active polysaccharides according to a preferred embodiment of this invention.

The present invention relates to a process for preparing a polysaccharide-based extract from *Ganoderma lucidum* or *Ganoderma tsugae*.

Particularly, the invention relates to a use of the polysaccharide-based extract of Ganoderma herbal material in an orally active medicinal product which has immunopotentiating and antitumoral effects, such as enhancement of the concanvalin A-stimulated splenocyte mitogenic activity, natural killer cell activity, granulocyte/macrophage colony stimulating activity, antibody response to bacterial polysaccharide antigen, and antitumoral activity against mouse LL/2 Lewis lung carcinoma.

In accordance with the present invention, a process for preparing a polysaccharide-based extract consists essentially the steps of:

(1) subjecting a raw ganoderma herbal material to an alcohol treatment to remove a major portion of non-polysaccharide ingredients to obtain a polysaccharide-rich product;

(2) using water of an elevated temperature as an extracting agent for the polysaccharide-rich product to obtain a supernatant solution; and (3) adding an alcohol into the supernatant solution to precipitate the polysaccharide-based extract.

Preferably, the alcohol used to remove the major portion of non-polysaccharide ingredients in step (1) is methanol or ethanol, while the alcohol used in step (3) to precipitate the polysaccharide-based extract is ethanol.

In a preferred embodiment of this invention, the temperature of the water in step (2) is the boiling temperature of water.

In the present invention, the preparing process further comprises a step of treating the polysaccharide-based extract with a deproteinizing agent so as to remove proteineous portions therefrom, and the result is named as Galu(C). The deproteinizing agent is a solvent mixture capable of removing protein from the polysaccharide-based extract. One example of the solvent mixture in the preferred embodiment is a mixture of chloroform and 1-butanol.

For comparison in immunopotentiating and antitumoral effects with the polysaccharides extracted by traditional alkaline methods of using sodium hydroxide, the ganoderma polysaccharides Galu(C) were further treated with 0.5N NaOH to obtain a product hereinafter referred to as ganoderma polysaccharides Galu(N).

To investigate the pharmacological effects of the ganoderma polysaccharide Galu(C) in immunopotentiating and antitumoral activities, experiments for determining the concanvalin A-stimulated splenocyte mitogenic activity, the natural killer activity, the granulocyte/macrophage colony stimulating activity, the IgA antibody response, and the antitumoral activity have been performed.

Concanvalin A (ConA) as referred herein is a mitogen that induces mitosis in T cells. Therefore, the response of T cells to ConA is a good marker of the function of T cells.

Natural killer (NK) cells as referred herein are non-T, non-B lymphocytes, which would destroy the antibody-coated target cells. The destruction by NK cells is called antibody-dependent cell-mediated cytotoxicity (ADCC). It has been reported that NK cells are able to kill certain tumor cells.

Granulocyte/macrophage colony stimulating factor (GM-CSF) as referred herein is a cytokine, which helps to recruit effector cells in infection by acting on bone marrow cells to stimulate myelopoiesis, the production of macrophages and granulocytes, and to stimulate the production of dendritic cells from bone marrow precursors.

IgA, an isotype of the immunoglobulin, is the principal isotype in secretion. It is believed that the primary functional role of IgA antibodies is to protect epithelial surfaces from infectious agents and therefore provides the first line of defense against a wide variety of pathogens.

From the experimental data of this invention, the inventor surprisingly found that the ganoderma polysaccharides Galu (C) of this invention have the ability of enhancing of immunopotentiating activity, i.e. the concanvalin A-stimulated splenocyte mitogenic activity, the natural killer activity and the granulocyte/macrophage colony stimulating activity via alimentary route. The inventor also surprisingly found that the oral activities of ganoderma polysaccharides Galu(C) for immunopotentiating function are more efficacious than that of ganoderma polysaccharides Galu(N).

It is believed that the presence of sodium hydroxide solution in the extraction of polysaccharide gives rise to the smaller dimension of the polysaccharide molecules in the resultant extract. The polysaccharide molecules of smaller dimension in the ganoderma extract of the prior methods evidently account for the unavailability in reporting the antitumoral and immunomodulating effectiveness of the ganoderma extract when it is administered orally.

In another study conducted by the inventor concerning IgA antibody response to subcutaneously administered bacterial polysaccharide antigen, the result demonstrates that the effect of orally-administered ganoderma polysaccharides of this invention on blood IgA level induced by subcutaneously challenging with Pneumovax 23 in BALB/c mice was evidently enhanced. Therefore, the ganoderma polysaccharides prepared by this invention are capable of enhancing the IgA level so as to improve the first line of defense against a wide variety of pathogens.

In accordance with the present invention, the polysaccharides of this invention are also capable of enhancing antitumoral activity against mouse LL/2 Lewis lung carcinoma. The C57BL/6 male mice were transplanted with LL/2 Lewis lung carcinoma in solid form, and then orally fed with polysaccharides of this invention. The results show that the life-span of the mice transplanted with $2 \times 10^5$ LL/2 Lewis lung carcinoma has been prolonged by over 40% when the polysaccharides of this invention are taken in the dose of 50 mg/Kg/day.

The experiments performed in accordance with the present invention clearly demonstrate that ganoderma polysaccharides-based extract is orally active in immuno-potentiating and antitumoral effects. The present invention therefore provides an application of ganoderma polysaccharides in tumor/cancer treatment and health protection.

EXAMPLES OF THE INVENTION

The following Examples are given for the purpose of illustration only and are not intended to limit the scope of the present invention.

Example 1

Extraction and Isolation of Polysaccharides 5 kg of the dried and cut raw Ganoderma herbs was extracted with methanol or ethanol overnight, and then separated by centrifugation. The methanol or ethanol extraction process was carried out three times. The precipitate was dried in a hot air oven, and then added with deionized water and held at 4° C. overnight to subject the precipitate to cold infiltration. The resultant mixture was heated to 100° C. and boiled for two hours. A supernatant solution was obtained by centrifuging the mixture, and the supernatant solution was then subjected to a chloroform (1/5 volume) and 1-butanol (1/15 volume) de-proteinizing process for three times. Thereafter, the Ganoderma polysaccharide was recrystallized from the deproteinized supernatant solution using ethanol. The orally active Ganoderma polysaccharides Galu (C) were obtained therefrom by lyophilizing the re-dissolved polysaccharide-containing solution. The isolation flowchart is as shown in FIG. 1. For comparison with conventional alkaline extraction of these polysaccharides, the Ganoderma polysaccharides Galu(C) were solubilized in 0.5N NaOH and stirred overnight at room temperature, then adjusted to pH 7.0 and dialyzed overnight at 4° C. The resultant polysaccharide-containing solution was subjected to lyophilization so as to obtain Galu(N).

Figure 2:
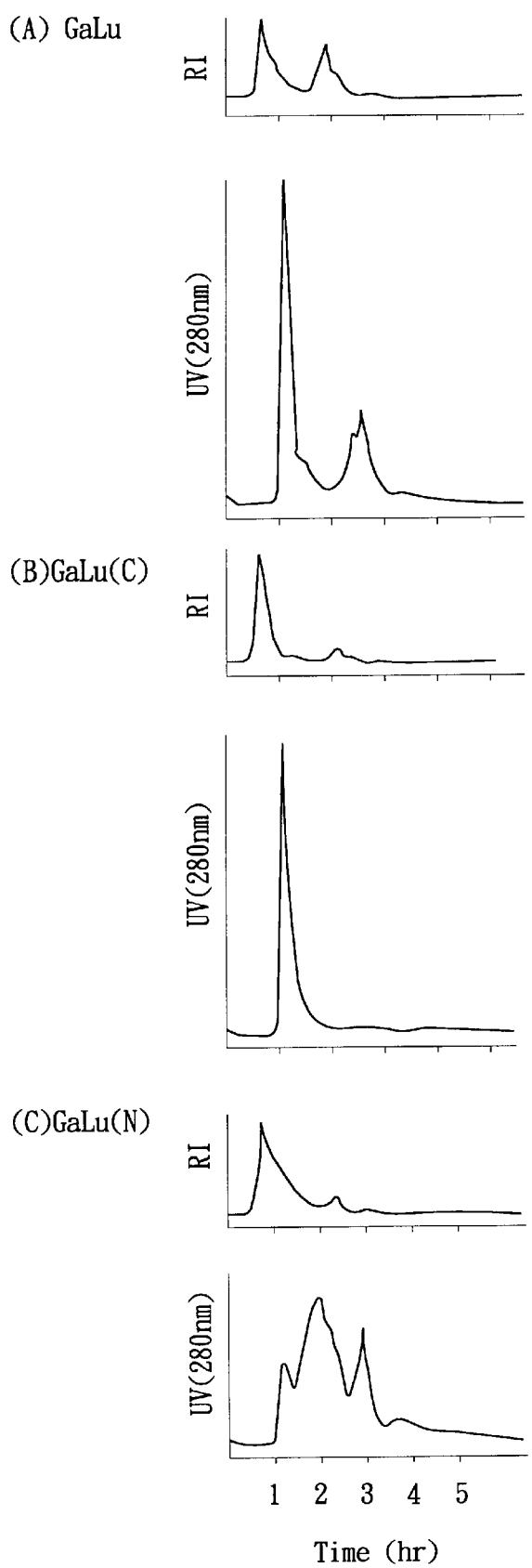
FIG. 2 shows chromatograms illustrating elution profiles of the orally-active polysaccharides according to the present invention.

In FIG. 2, a number of chromatograms are shown to illustrate elution profiles of the polysaccharide Galu(C) and Galu(N). In proceeding with the gel chromatographic analysis, the polysaccharides were solubilized and applied to a 1.0 cm×120 cm Sephacryl S-200 HR gel filtration column. These chromatogragrams were monitored by both UV (O.D. 280 nm, 111B Gilson, Wis.) and RI (reflex index, ERC-7525 Japan) spectrophotometer. After the de-proteinizing process, the peak of smaller molecular weight was eliminated (FIGS. 2A and 2B). As shown in FIG. 2C, the Galu(C), a Ganoderma polysaccharide with higher molecular weight, has evidently been broken into pieces by sodium hydroxide solution so as to form a number of Ganoderma polysaccharides with a lower molecular weight, i.e. Galu(N).

Example 2
Proliferative Response of Mouse Lymphocytes to Concanavalin A

Figure 3:
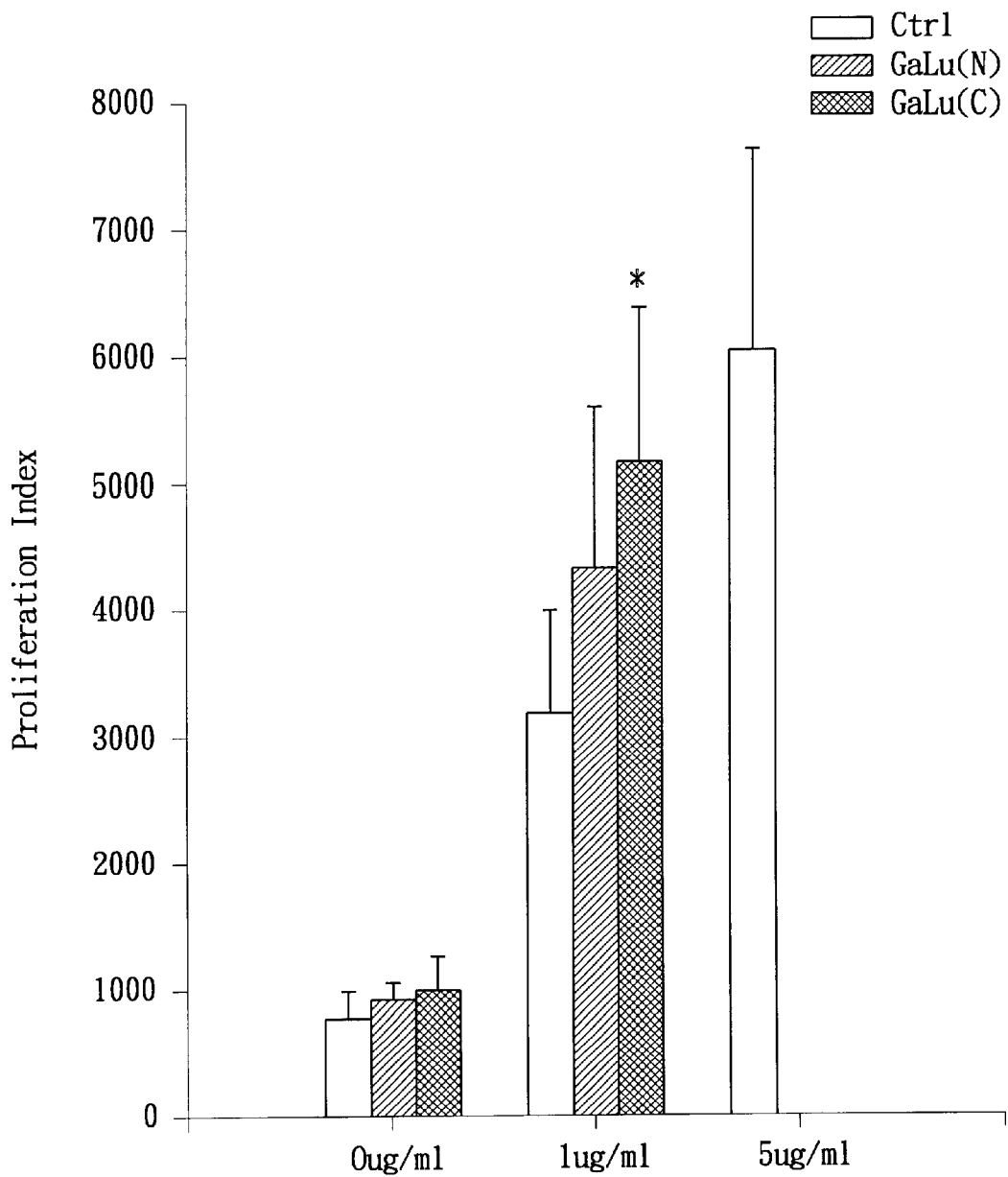
FIG. 3 is a bar graph illustrating the proliferative response of mouse lymphocytes to concanavalin-A when mice have been treated with the orally active polysaccharides according to the present invention.

Proliferative Response of Mouse Lymphocytes to Concanavalin A is determined by MTT assay. Ganoderma polysaccharide was administered orally by food-intake (10 mg/Kg/day) for 3 days to male BALB/c mice. The mice were then sacrificed for experiment. Fresh splenocytes ($2 \times 10^6$ cells/ml) were isolated and suspended in a RPMI 1640 medium with 0.1 mM nonessential amino acid, $2 \times 10^{-6}$M 2-mercaptoethanol, 100 units/ml benzyl-penicillin, 100 µg/ml streptomycin, 10% heat-inactivated fetal calf serum, and a final concentration of 1 µg/ml of concanavalin A (Sigma, Mo.). 225 µl was then added to each well of flat-bottomed microplates (Costar, N.Y.) and were incubated for 3 days at 37° C. in a humidified atmosphere containing 5% $CO_2$. 25 µl of 5 mg/ml tetrazolium salt MTT (3-(4,5-dimethylthiazol-2-yl)-2,5-diphenyl tetrazolium bromide) (Sigma, Mo.) was subsequently added to each well for 4 hours, and 100 µl lysis solution (20% SDS/50% DMF) was then added overnight. The absorption of O.D. 570 nm was measured by using a microplate reader (Bio-rad). These experiments were performed in quadruplicate. As shown in FIG. 3, when polysaccharide Galu(C) was orally-administered, the proliferative response of mouse lymphocytes to concanavalin A was obviously stronger than that when polysaccharide Galu(N) was orally-administered at the dose of 10 mg/Kg/day in BALB/c mice.

Example 3
Natural Killer Cytotoxicity Assay

The natural killer activity was assessed by a BCECF fluorescence retention assay. The mouse lymphoma cell line, YAC-1, was used as target cells. The target cells were generally maintained in RPMI 1640 medium with 10% FCS, in a 5% $CO_2$ incubator at 37° C. The target cells were washed twice with RPMI 1640 medium and adjusted to a concentration of $1 \times 10^6$ cells/ml in RPMI 1640 medium with 5% heat-inactivated FCS for later use. The target cells are labeled with 5 µM of calcein AM (Molecular probes, OR, USA) for 30 min at 37° C. Calcein AM is a non-polar dye, which has been designed to be taken by cells as ester and subsequently hydrolyzed by internal esterase. The hydrolyzed product is relatively impermeable to cell membranes and is thus retained in target cells for measuring the cytotoxicity. After washing three times with cold RPMI 1640 medium, these target cells were resuspended in a concentration of $1 \times 10^6$ cells/ml in RPMI 1640 medium with 5% FCS. Spleen cells isolated from the BALB/c mice administered (10 mg/Kg) or not administered with the ganoderma polysaccharides were used as effector cells. The spleen cells were depleted of adherent cells by incubation in plastic Petri dishes in RPMI 1640 medium with 5% FCS for 1 hour at 37° C. in 5% $CO_2$ atmosphere. 0.1 ml of the effector cells of non-adherent spleen cells were mixed with 0.1 ml target cells at ratios of 30:1 and 15:1 (effector cells to target cells (E:T)) in the microwells of a round-bottomed 96-well microplate (Nunclon, Nunc, Denmark). After incubating for 4 hrs, 5 µl FluoroQuench was added to each well for quenching the calcein AM residue outside the cells. The fluorescence dye retained inside the cells in each well was measured by Spectrofluorimeter Cyto 2300 (Millipore, Bedford, Mass., USA) with an excitation setting of 496 nm and emission setting of 520 nm. The natural killer cytotoxic activity was expressed as follows:

% cytolysis=[1−(experimental fluorescence−background fluorescence)/(maximal fluorescence−background fluorescence)]×100

Figure 4:
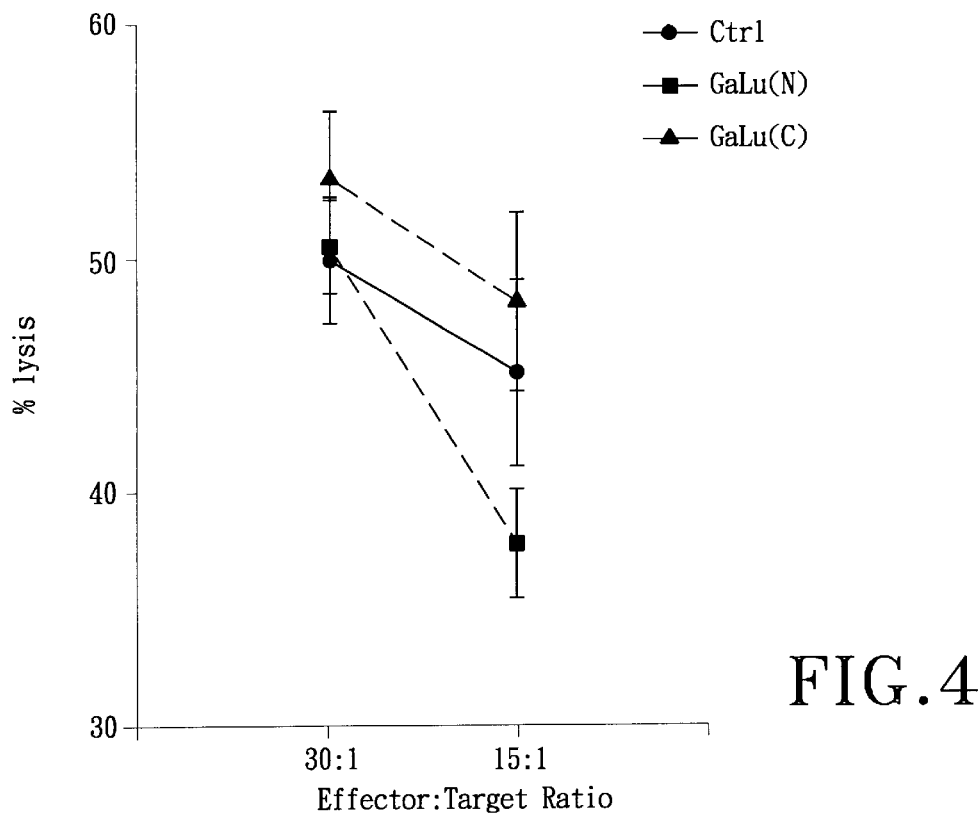
FIG. 4 is a graph showing the natural killer cytotoxicity bioassay conducted with the splenocytes of mice orally administered with the active polysaccharides according to the present invention.

These experiments were performed in quadruplicate. As shown in FIG. 4, the natural killer activity of BALB/c mice orally-administered with polysaccharide Galu(C) was significantly stronger than that when mice were orally-administered with polysaccharide Galu(N) at the dose of 10 mg/Kg/day.

Example 4
Granulocyte/Macrophage Colony Stimulating Activity

Figure 5:
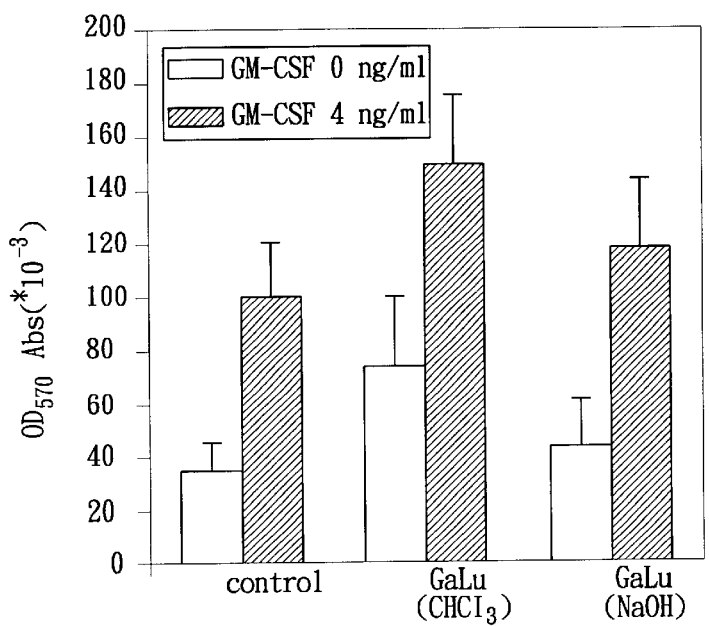
FIG. 5 is a bar graph illustrating the proliferative response of mouse bone marrow progenitor cells to granulocyte/macrophage colony stimulating factor in which the mice have been treated with the orally active polysaccharides according to the present invention.

The proliferative response of granulocyte/macrophage colony was evaluated using MTT assay. Ganoderma polysaccharide Galu(C) and Galu(N) were administered orally by food-intake (10 mg/Kg/day) for 3 days to male BALB/c mice. The mice were then sacrificed by cervical dislocation for experiment. Femoral bone marrow cells as a source of granulocyte/macrophage progenitor cells were obtained by flushing the marrow cavity with RPMI 1640 medium using a 26-gauge needle. The cells ($4 \times 10^5$ cells/ml) were cultured in RPMI 1640 medium with $5 \times 10^{-6}$ M 2-mercaptoethanol, 100 units/ml benzylpenicillin, 100 µg/ml streptomycin, 5% heat-inactivated FCS, and a final concentration of 4 ng/ml of mouse recombinant granulocyte/macrophage colony stimulating factor. 225 µl of this medium was then added to each well of flat-bottomed microplates (Costar) and incubated for 3 days at 37° C. in a humidified atmosphere containing 5% $Co_2$. 130 µl of the supernatant in each well was removed and 25 µl MTT was subsequently added to each well for 4 hrs. 100 µl lysis solution (20% SDS/50% DMF) was added to each well overnight. The absorption of O.D. 570 nm was measured by using a microplate reader (Bio-rad). These experiments were performed in quadruplicate. As shown in FIG. 5, the proliferative response of mouse granulocyte/macrophage progenitor cells to mouse recombinant granulocyte/macrophage colony stimulating factor was obviously enhanced when the mice were orally administered with polysaccharide Galu(C) than with Galu(N) in the dose of 10 mg/Kg/day in BALB/c mice.

Example 5
Enhancement of Antibody Response to Bacterial Polysaccharide Antigen by Orally Food-Intake of Ganoderma Polysaccharide Protective immunity against the pathogen *Streptococcus pneumoniae* is mediated by specific antibodies to the capsular polysaccharides. Pneumococcus vaccine was used for systemic immunization and included 23 of the most prevalent serotypes. The vaccine is efficacious in healthy adults. However, elderly and patients with immunodeficiencies respond poorly to the capsular polysaccharide and consequently account for most of the invasive infectious diseases.

Although pneumococcal vaccines have been given via the systemic route and induce immunity by IgG production, the pneumococcus initially invades the host via the mucosal surface. Thus, the pneumococcal polysaccharide specific IgA response is a renewed effort to develop a more efficacious vaccination.

Figure 6:
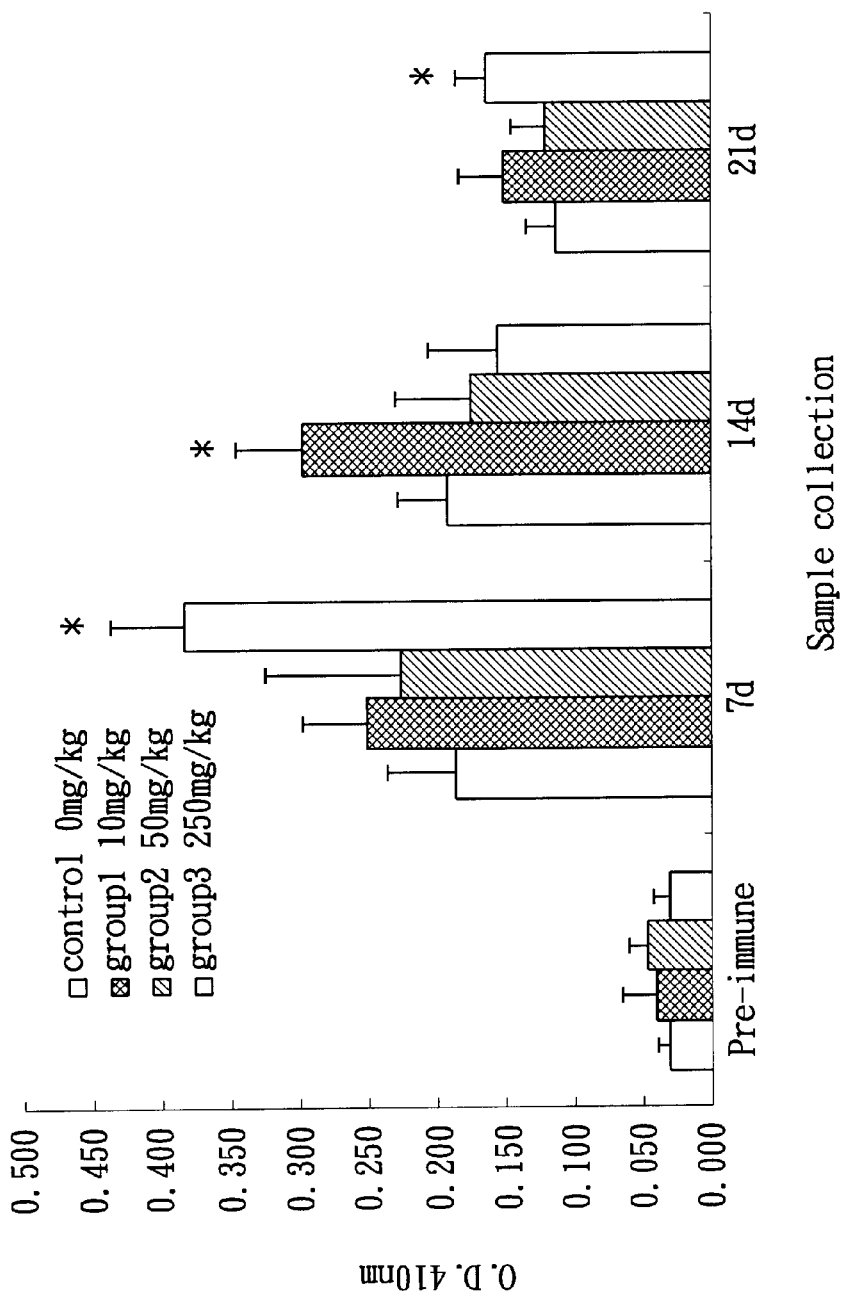
FIGS. 6 and 7 are bar graphs illustrating the serum IgA titers to subcutaneous immunization of mice with pneumococcal polysaccharide elevated by the orally active polysaccharides according to the present invention.
Figure 7:
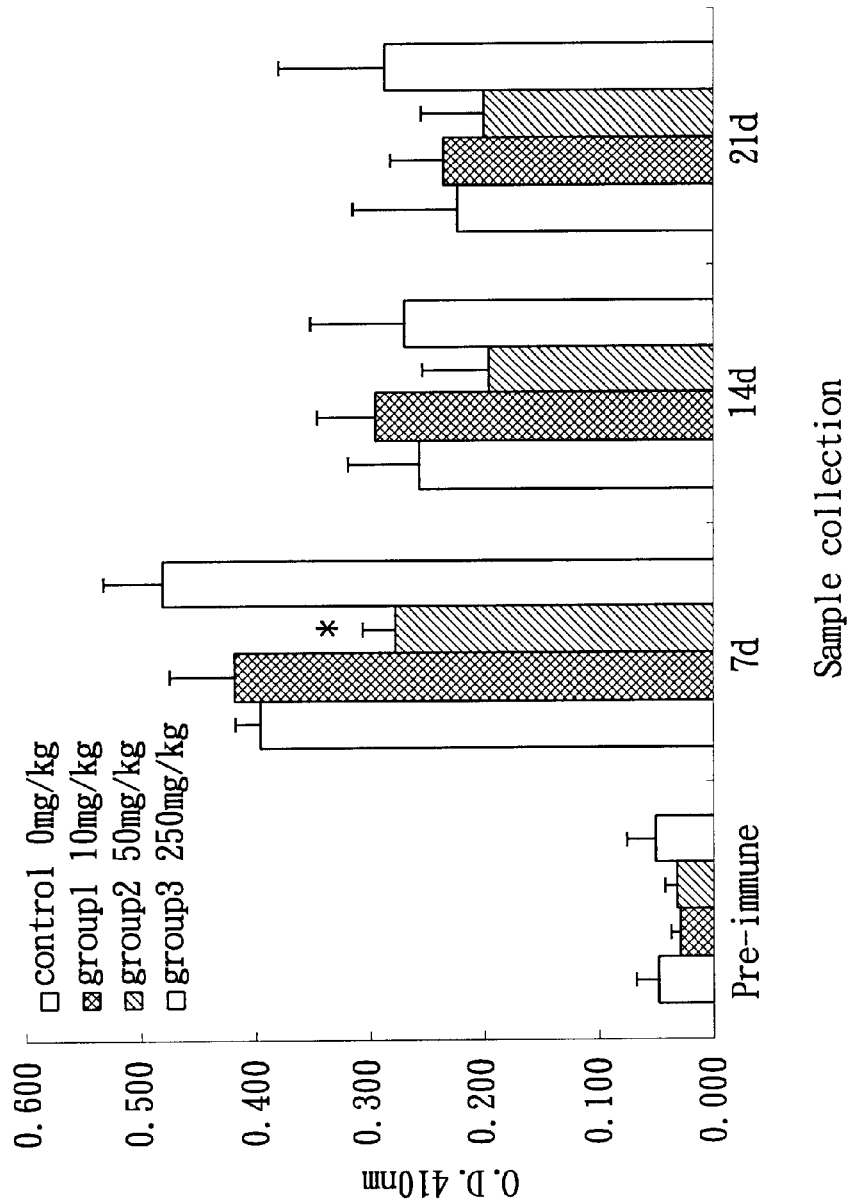

The effectiveness of orally food-intake ganoderma polysaccharide in eliciting the antibody response to subcutaneously administered pneumococcal vaccine was examined. Male BALB/c mice at 8–14 weeks of age were used for this study and kept in a specific pathogen free environment in the Animal Center of National Yang-Ming University. Subcutaneous immunization was carried out by injection of a single dose of 2.3 $\mu$g/mouse of Pneumovax 23 (Merck & Co., Inc. West point, Pa., USA). Preimmune serum was obtained from eyes before Pneumovax immunization. Then, the ganoderma polysaccharides were given orally in a solution as of the next day to day 21. The serum samples were collected from eyes on day 7, 14, and 21 and assayed for IgG and IgA anti-Pneumovax 23 antibody isotype by ELISA. Costar microplate were precoated with 2.3 $\mu$g Pneumovax 23 in 50 $\mu$l PBS at 4° C. overnight. After rinsing three times with PBS containing 0.05% Tween 20, wells were blocked by PBS containing 1% bovine albumin for 2 hrs and were then rinsed six times with PBS containing 0.05% Tween 20. Samples were tested at a dilution of 1:100 and 1:400. Plates were incubated at room temperature for 2 hrs and the bound antibodies were detected by alkaline phosphatase conjugated goat anti-mouse IgG or IgA antibodies. p-Nitrophenyl phosphate was used for color development. Titers were recorded as the serum dilution of 1:100 or 1:400 which gave an absorbance of 410 nm. As shown in FIG. 6, serum IgA titers of the mice subcutaneously immunized with pneumococcal polysaccharide were significantly elevated by the orally-active Ganoderma polysaccharides on day 7 at the dose of 250 mg/Kg, and on day 14 at the dose of 10 mg/Kg. In contrast with serum IgG, the Ganoderma polysaccharides did not elevate the IgG titers throughout the polysaccharide intake period (FIG. 7). This embodiment demonstrated that the enhancement of IgA antibody responses to subcutaneously administrated bacterial polysaccharide antigen takes place in the event of oral-intake of the Ganoderma polysaccharides. This finding suggests that Ganoderma polysaccharides extracted by the protocol of this invention might enhance the antigen-specific antibody responses, and might offer a more efficacious vaccination for the elderly or patients with immunodeficiencies.

Example 6

Antitumor Activity Against Mouse LL/2 Lewis Lung Carcinoma

The LL/2 Lewis lung carcinoma was maintained in solid form by serial s.c. transplantation in syngeneic C57BL/6 male mice. When LL/2 Lewis lung carcinoma reached a size of approximately 10 mm diameter, the tumor tissue was excised and trimmed to be free of necrotic area. Cell suspension was then prepared by mechanical means in Hank's balance salt solution (HBSS). The viability was determined by the Trypan-blue exclusion test. For the therapeutic experiments, C57BL/6 mice received s.c. injection of $2\times10^5$ Lewis lung carcinoma cells/0.2 ml HBSS/mouse on day 0. After transplanting the tumor tissue, mice were randomly assigned to experimental and control groups. There were 6–8 mice in each group. Ganoderma polysaccharides were administered orally by food-intake (250, 50, 10 mg/Kg/day) starting on day 5 and ending with the termination of the experiment. The therapeutic response was determined by the life-span extension of the polysaccharide-treated mice compared to that of the untreated mice. As shown in Table 1-I, life-span of the tumor-bearing ($2\times10^5$ LL/2 cells) mice was prolonged over 40% at the dose of 50 mg/Kg/day (*P<0.01). In other experiments, life-span of the tumor-bearing ($1\times10^6$ LL/2 cells) mice was also prolonged over 19% at the same dose, as shown in Table 1-II.

TABLE 1-I

| Treatment | Dose (mg/Kg × day) | Mean survival ± S.D. (Days) | ILS (%) |
|---|---|---|---|
| Control | | 40.1 ± 8.3 | 100 |
| GPS | 250 × 36 | 44.4 ± 15.3 | 111 |
| | 50 × 36 | 56.5 ± 12.8 | 141* |
| | 10 × 36 | 45.3 ± 9.9 | 113 |

The C57BL/6 mice were implanted with $2 \times 10^5$ Lewis lung carcinoma. The sign "*" demonstrates that p < 0.01.

TABLE 1-II

| Treatment | Dose (mg/Kg × day) | Mean survival ± S.D. (Days) | ILS (%) |
|---|---|---|---|
| Control | | 32.0 ± 5.9 | 100 |
| GPS | 50 × 36 | 38.1 ± 8.8 | 119* |
| | 10 × 36 | 33.8 ± 7.9 | 106 |
| | 2 × 36 | 32.9 ± 7.5 | 103 |
| | 0.4 × 36 | 33.1 ± 10.5 | 103 |

The C57BL/6 mice were implanted with $2 \times 10^5$ Lewis lung carcinoma. The sign "*" demonstrates that p < 0.05.

While the invention has been described with reference to the above specific embodiments, it should be recognized that various modifications and changes, which will be apparent to those skilled in the relevant art, may be made without departing from the spirit and scope of the invention.

I claim:

1. An oral pharmaceutical composition comprising a polysaccharide-based extract prepared from a process which consists essentially of:
   (1) subjecting a raw ganoderma herbal material to an alcohol treatment to remove a major portion of non-polysaccharide ingredients to obtain a polysaccharide-rich product;
   (2) using water at an elevated temperature as an extracting agent for said polysaccharide-rich product to obtain a supernatant solution;
   (3) adding an alcohol to said supernatant solution to precipitate said polysaccharide-base extract; and
   (4) treating said polysaccharide-based extract with a deproteinizing agent to remove proteinaceous portions therefrom.

2. The oral pharmaceutical composition according to claim 1, wherein in step (1), the alcohol used in said alcohol treatment is selected from a group consisting of methanol and ethanol.

3. The oral pharmaceutical composition according to claim 2, said composition providing immunopotentiating and antitumoral effects.

4. The oral pharmaceutical composition according to claim 1, wherein in step (2), said elevated temperature is the boiling temperature of water.

5. The oral pharmaceutical composition according to claim 4, said composition providing immunopotentiating and antitumoral effects.

6. The oral pharmaceutical composition according to claim 1, said composition providing immunopotentiating and antitumoral effects.

* * * * *